US00PP20945P2

(12) United States Plant Patent
Kuga

(10) Patent No.: US PP20,945 P2
(45) Date of Patent: Apr. 27, 2010

(54) ***PETUNIA* PLANT NAMED 'OSCOPET2'**
(50) Latin Name: *Petunia×hybrida*
Varietal Denomination: Oscopet2

(75) Inventor: Takanori Kuga, Katanobu Asakura (JP)

(73) Assignee: De Zonnebloem Breeding B.V., De Kwakel (NL)

( * ) Notice: Subject to any disclaimer, the term of this patent is extended or adjusted under 35 U.S.C. 154(b) by 0 days.

(21) Appl. No.: 12/313,685

(22) Filed: Nov. 21, 2008

(51) Int. Cl.
*A01H 5/00* (2006.01)

(52) U.S. Cl. ..... Plt./356
(58) Field of Classification Search ..... Plt./356
See application file for complete search history.

*Primary Examiner*—June Hwu
(74) *Attorney, Agent, or Firm*—C. A. Whealy

(57) ABSTRACT

A new and distinct cultivar of *Petunia* plant named 'Oscopet2', characterized by its upright and outwardly spreading plant habit; moderately vigorous growth habit; narrow leaves; star-shaped purple-colored flowers; and relative tolerance to low temperatures.

2 Drawing Sheets

Botanical designation: *Petunia×hybrida.*
Cultivar denomination: 'Oscopet2'.

BACKGROUND OF THE INVENTION

The present invention relates to a new and distinct cultivar of *Petunia* plant, botanically known as *Petunia×hybrida* and hereinafter referred to by the name 'Oscopet2'.

The new *Petunia* plant is a product of a planned breeding program conducted by the Inventor in Higashiomi, Shiga, Japan. The objective of the breeding program is to create new cold-tolerant *Petunia* cultivars with small leaves and attractive flower coloration.

The new *Petunia* plant originated from a cross-pollination made by the Inventor in March, 2004 in Asakura-city, Fukuoka, Japan of a proprietary selection of *Petunia×hybrida* identified as code number peku34, not patented, as the female, or seed, parent with a proprietary selection of *Petunia×hybrida* identified as code number peku72, not patented, as the male, or pollen, parent. The new *Petunia* was discovered and selected by the Inventor as a single flowering plant within the progeny of the stated cross-pollination in a controlled environment in Asakura-city, Fukuoka, Japan in May, 2005.

Asexual reproduction of the new *Petunia* plant by terminal cuttings in a controlled environment in Asakura-city, Fukuoka, Japan since August, 2005, has shown that the unique features of this new *Petunia* plant are stable and reproduced true to type in successive generations.

SUMMARY OF THE INVENTION

Plants of the new *Petunia* have not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Oscopet2'. These characteristics in combination distinguish 'Oscopet2' as a new and distinct cultivar of *Petunia:*

1. Upright and outwardly spreading plant habit.
2. Moderately vigorous growth habit.

3. Narrow leaves.
4. Star-shaped purple-colored flowers.
5. Relatively tolerant to low temperatures.

Plants of the new *Petunia* can be compared to plants of the female parent selection. Plants of the new *Petunia* differ primarily from plants of the female parent selection in the following characteristics:

1. Plants of the new *Petunia* have narrower leaves than plants of the female parent selection.
2. Plants of the new *Petunia* have smaller flowers than plants of the female parent selection.

Plants of the new *Petunia* can be compared to plants of the male parent selection. Plants of the new *Petunia* differ primarily from plants of the male parent selection in the following characteristics:

1. Plants of the new *Petunia* have narrower leaves than plants of the male parent selection.
2. Flowers of plants of the new *Petunia* have sharper petal apices than plants of the male parent selection.

Plants of the new *Petunia* can also be compared to plants of 'Oostchang', not patented. In side-by-side comparisons conducted in Asakura-city, Fukuoka, Japan, plants of the new *Petunia* and 'Oostchang' differed primarily in the following characteristics:

1. Plants of the new *Petunia* were more outwardly spreading than plants of 'Oostchang'.
2. Leaves of plants of the new *Petunia* were more viscid than leaves of plants of 'Oostchang'.
3. Plants of the new *Petunia* and 'Oostchang' differed in flower color as flowers of plants of 'Oostchang' had pink-colored flowers.

BRIEF DESCRIPTION OF THE PHOTOGRAPHS

The accompanying colored photographs illustrate the overall appearance of the new *Petunia*, showing the colors as true as it is reasonably possible to obtain in colored reproductions of this type. Colors in the photographs may differ slightly from the color values cited in the detailed botanical description which accurately describe the colors of the new *Petunia.*

The photograph on the first sheet comprises a side perspective view of a typical flowering plant of 'Oscopet2' grown in a container.

The photograph on the second sheet is a close-up view of typical flowers and leaves of 'Oscopet2'.

DETAILED BOTANICAL DESCRIPTION

The aforementioned photographs and following observations, measurements and values describe plants grown in De Kwakel, The Netherlands under commercial practice during the summer in an outdoor nursery. During the production of the plants, day temperatures ranged from 14° C. to 30° C. and night temperatures ranging from 5° C. to 16° C. Plants were pinched one time about two weeks after planting and had been growing for three months when the photographs and description were taken. In the following description, color references are made to The Royal Horticultural Society Colour Chart, 2001 Edition, except where general terms of ordinary dictionary significance are used.

Botanical classification: *Petunia×hybrida* 'Oscopet2'.

Parentage:

*Female, or seed, parent*.—Proprietary selection of *Petunia×hybrida* identified as code number peku34, not patented.

*Male, or pollen, parent*.—Proprietary selection of *Petunia×hybrida* identified as code number peku72, not patented.

Propagation:

*Type*.—By terminal cuttings.

*Time to initiate roots, summer*.—About seven days at temperatures of 22° C.

*Time to initiate roots, winter*.—About ten days at temperatures of 19° C.

*Time to produce a rooted young plant, summer*.—About three weeks at temperatures of 21° C.

*Time to produce a rooted young plant, winter*.—About four weeks at temperatures of 18° C.

*Root description*.—Fibrous; white to light brown in color.

*Rooting habit*.—Freely branching; dense.

Plant description:

*Plant and growth habit*.—Upright and outwardly spreading plant habit. Freely branching habit with about 13 lateral branches developing per plant; pinching enhances lateral branch development. Moderately vigorous growth habit.

*Plant height*.—About 21.4 cm.

*Plant diameter*.—About 36.7 cm.

Lateral branch description:

*Length*.—About 18.2 cm.

*Diameter*.—About 1.5 mm.

*Internode length*.—About 1.6 cm.

*Strength*.—Moderately strong.

*Aspect*.—Upright to outwardly.

*Texture*.—Densely pubescent; slightly viscid.

*Color*.—Close to 143A to 143B.

Foliage description:

*Arrangement*.—Alternate, simple.

*Length*.—About 4.1 cm.

*Width*.—About 1.1 cm.

*Shape*.—Narrowly ovate.

*Apex*.—Acute.

*Base*.—Attenuate.

*Margin*.—Entire.

*Texture, upper and lower surfaces*.—Pubescent; slightly viscid.

*Venation pattern*.—Pinnate.

*Color*.—Developing leaves, upper and lower surfaces: Close to 144A; towards the base, close to 144C to 144D. Fully developed leaves, upper surface: Between 137C and 138A; venation, close to 144A. Fully developed leaves, lower surface: Close to 146C; venation, close to 144A to 144B.

*Petioles*.—Length: About 8 mm. Diameter: About 1 mm. Texture, upper and lower surfaces: Pubescent. Color, upper and lower surfaces: Close to 144A to 144B.

Flower description:

*Flower arrangement and habit*.—Single salverform flowers arising from leaf axils. Freely flowering habit with usually about 170 flowers developing per plant. Flowers face upright to outwardly.

*Fragrance*.—Not detected.

*Time to flower/natural flowering season*.—Plants of the new *Petunia* initiate and develop flowers about three months after planting. Plants flower continuously in The Netherlands from June until frost.

*Flower longevity*.—Individual flowers last about seven days on the plant; flowers not persistent.

*Flower diameter*.—About 3.3 cm.

*Flower length (depth)*.—About 2.1 cm.

*Flower bud*.—Shape: Narrowly oblong. Length: About 1.4 cm. Diameter: About 5 mm. Color: Close to N186A to N186B.

*Corolla*.—Arrangement: Five petals fused at the base and opening into a flared trumpet. Petal length from throat: About 3.5 cm. Petal width: About 1.4 cm. Petal shape: Oblanceolate. Petal apex: Apiculate. Petal margin: Entire; undulate. Petal texture, upper and lower surfaces: Smooth, glabrous. Throat texture: Smooth, glabrous. Tube texture: Pubescent. Color: Petal, when opening, upper surface: Between N74A and N78A; venation, close to N186B. Petal, when opening, lower surface: Close to 77A; venation, close to 77A. Petal, fully opened, upper surface: Close to N78A to N78B; venation, close to N186B. Color becoming closer to N82A with development. Throat: Close to 85A to 85B; venation, close to N186B. Tube: Close to 79C; color becoming closer to N77C with development.

*Calyx*.—Arrangement: One star-shaped calyx tube with five sepals fused at the base per flower. Sepal length: About 1.7 mm. Sepal width: About 1.2 mm. Sepal shape: Lanceolate. Sepal apex: Acute. Sepal margin: Entire. Sepal texture, upper and lower surfaces: Pubescent. Color, upper surface: Close to 143A; towards the base, close to 144B. Color, lower surface: Close to 143A to 143B; towards the base, close to 144B.

*Peduncles*.—Length: About 1.8 mm. Diameter: About 1 mm. Strength: Moderately strong. Texture: Pubescent. Color: Close to 143B.

*Reproductive organs*.—Stamens: Quantity/arrangement: Five per flower. Anther shape: Reniform. Anther length: About 1.5 mm. Anther color: Close to 90C to 90D. Pollen amount: Scarce. Pollen color: Close to 115C. Pistils: Quantity: One per flower. Pistil length: About 7 mm. Style length: About 6 mm. Style color: Close to 144C. Stigma color: Close to 148A to 148B. Ovary color: Close to 144B. Seed/fruit: Seed and fruit development have not been observed on plants of the new *Petunia*.

Garden performance: Plants of the new *Petunia* have been observed to have good garden performance and to tolerate rain, wind and temperatures ranging from about −5° C. to about 35° C.

Pathogen/pest resistance: Plants of the new *Petunia* have not been observed to be resistant to pests and pathogens common to *Petunia.*

It is claimed:

1. A new and distinct *Petunia* plant named 'Oscopet2' as illustrated and described.

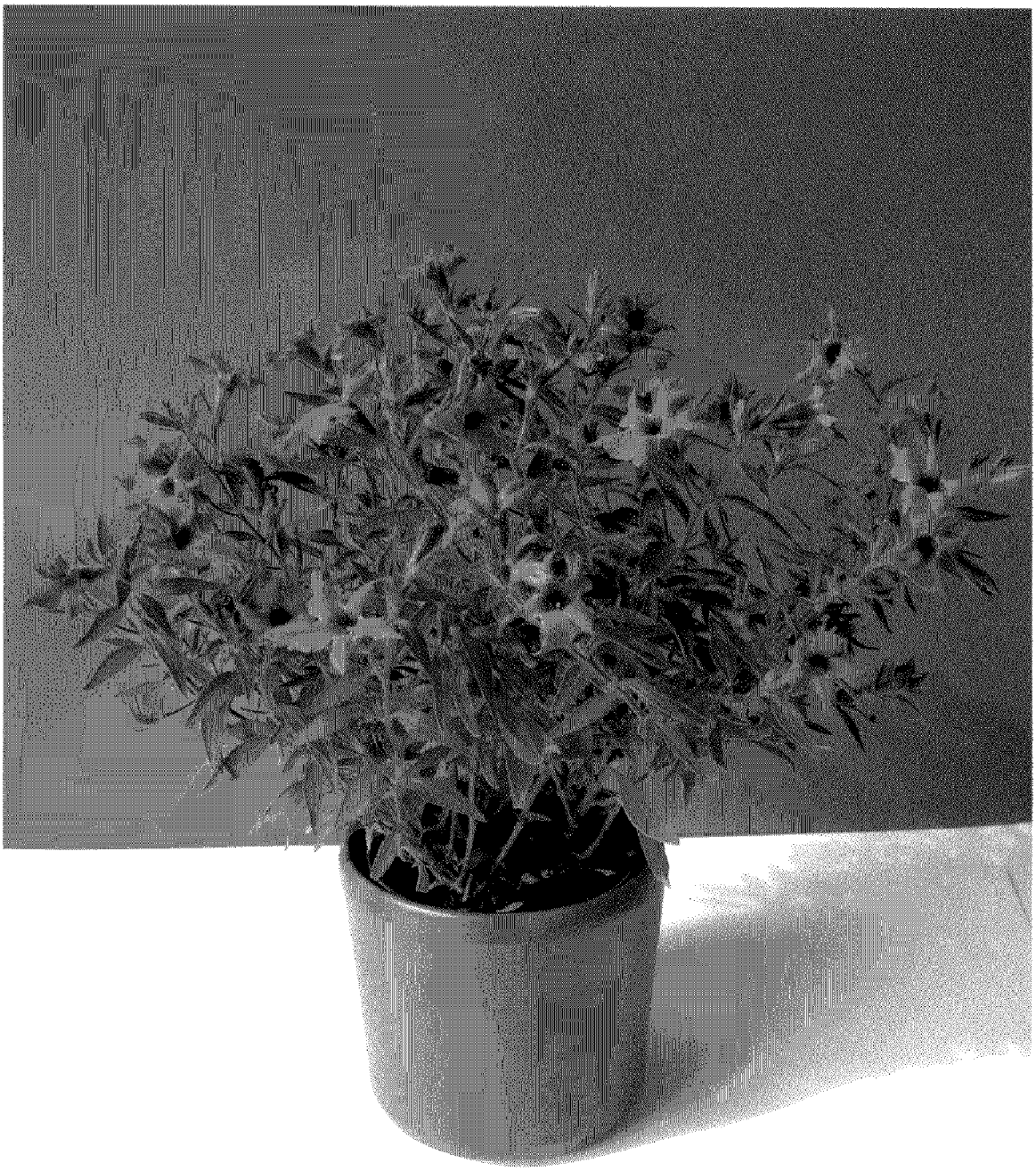

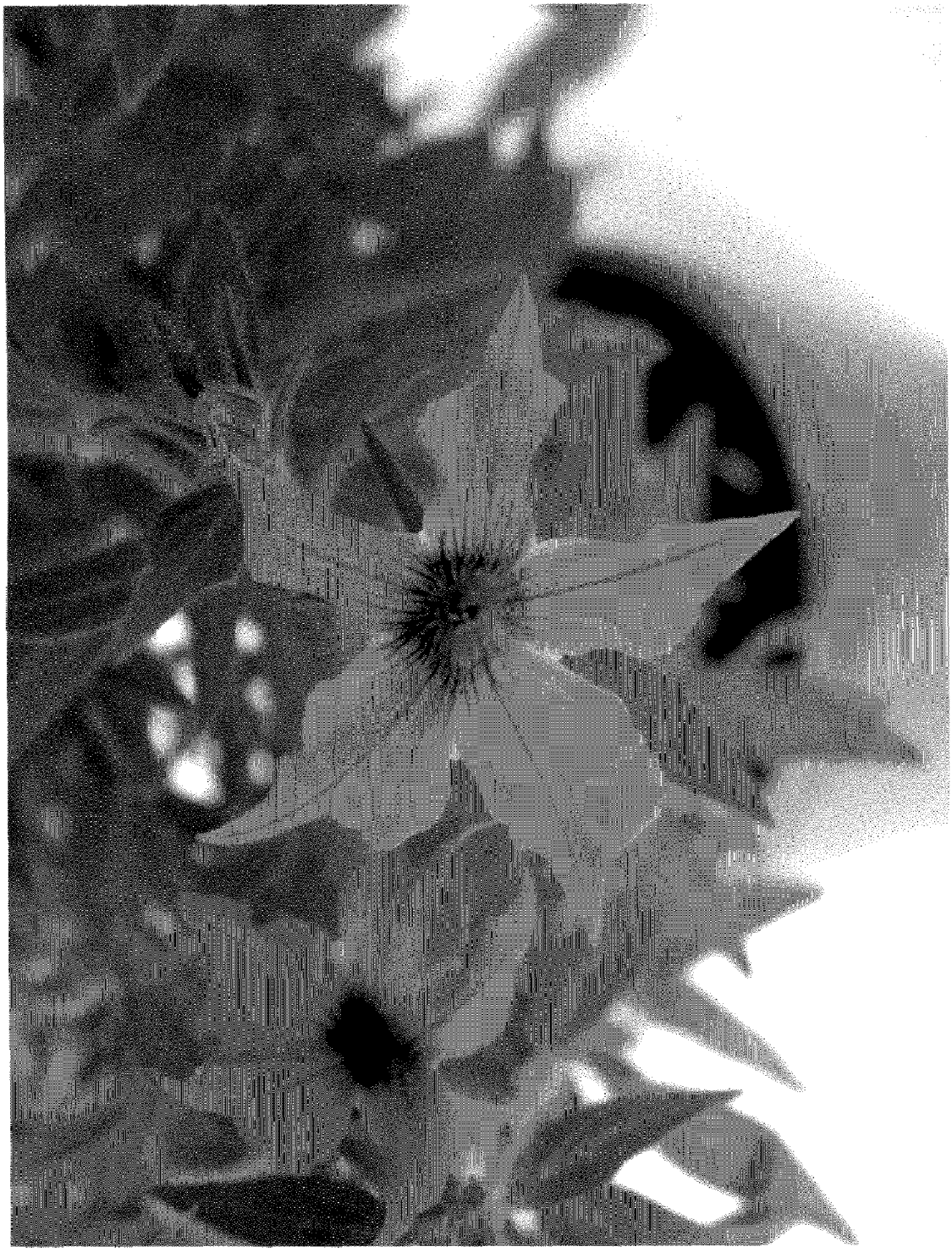

* * * * *